United States Patent [19]

Bush

[11] 4,400,531

[45] Aug. 23, 1983

[54] 4-VINYL-2-METHYLENE BUTANEDIOIC ACID COMPOUNDS

[75] Inventor: Rodney D. Bush, Cincinnati, Ohio

[73] Assignee: The Procter & Gamble Company, Cincinnati, Ohio

[21] Appl. No.: 290,907

[22] Filed: Aug. 7, 1981

[51] Int. Cl.$^3$ ............... C07C 69/593; C07C 101/20; C07C 121/30

[52] U.S. Cl. ............... 560/201; 260/465.4; 560/43; 560/155; 560/193; 526/322

[58] Field of Search ............... 560/193, 201, 155, 43; 260/465.4

[56] References Cited

U.S. PATENT DOCUMENTS

| | | |
|---|---|---|
| 2,153,987 | 4/1939 | Nicodemus et al. ............... 560/201 |
| 2,254,382 | 9/1941 | Neher ............... 560/201 X |
| 3,165,486 | 1/1965 | Johnson . |
| 3,280,067 | 10/1966 | Anagnostopoulos ............... 560/201 X |
| 3,773,810 | 11/1973 | Bellus ............... 560/201 X |
| 3,784,578 | 1/1974 | Swodenk et al. ............... 560/201 X |

OTHER PUBLICATIONS

Merck Index, 9th ed. (p. 688).
Akashi, Kogyo Kagaku Zasshi, 66: 127-9 (1963).
Akashi, Kogyo Kagaku Zasshi, 66 (12): 1909-12 (1963).

*Primary Examiner*—Natalie Trousof
*Assistant Examiner*—Vera C. Clarke
*Attorney, Agent, or Firm*—Steven J. Goldstein; Jack D. Schaeffer; Richard C. Witte

[57] ABSTRACT

4-Vinyl-2-methylenebutanedioic acid and its esters, as well as amide and nitrile analogs of these compounds, are disclosed. These compounds are capable of undergoing a rapid free radical cyclopolymerization reaction. The compounds, themselves, may be used as film-formers (for example, in paints or plastics) or may be used as groups pendant from a backbone, especially a low molecular weight backbone, to form other, more complex film-forming polymer precursor materials.

4 Claims, No Drawings

4-VINYL-2-METHYLENE BUTANEDIOIC ACID COMPOUNDS

TECHNICAL FIELD

The present invention relates to a class of 4-vinyl-2-methylenebutanedioic acid compounds, and their amide and nitrile derivatives, which undergo an unusual rapid free-radical cyclopolymerization reaction to form strong, durable films and coatings.

BACKGROUND OF THE INVENTION

The concurrently-filed patent application of Robbins and Bush, U.S. patent application Ser. No. 290,918, Agents for Preparing Cross-Linked Polymers and Paint and Plastic Compositions Containing Those Agents, describes the desirability of formulating paint, coating or plastic compositions which are based on in situ polymerization technology. Using this approach, a polymer precursor material, in an appropriate vehicle, is spread in a film and a cross-linking polymerization reaction is initiated in that film, for example by contact with oxygen in the air or by the addition of heat. Based on a proper selection of the polymer precursor (i.e., one which provides a sufficiently rapid, yet controlled, rate of polymerization with a desirable degree of cross-linking), the films formed can be significantly more durable than conventional film-forming compositions (e.g., paint). The present invention relates to 4-vinyl itaconic acid (beta-vinyl itaconic acid) compounds, specifically 4-vinyl-2-methylenebutanedioic acid and its esters, as well as amide and nitrile analogues of these compounds. The compounds undergo a rapid free-radical polymerization reaction (it is believed that this reaction utilizes a cyclopolymerization mechanism) and are, therefore, useful themselves in formulating film-forming compositions. They may also be used in synthesizing more complex film-forming polymer precursor materials.

BACKGROUND ART

Itaconic acid (methylenesuccinic acid), having the following formula, is well-known in the art (see, Merck Index, Ninth Edition, Merck & Co., Inc., 1976, page 688).

$$CH_2=C-COOH$$
$$|$$
$$CH_2-COOH$$

In addition, vinyl derivatives of itaconic acid, such as 1-vinyl itaconate (1-vinyl-2-methylenebutanedioic acid), and divinyl itaconate, have been disclosed. See, for example, Akashi, *Kogyo Kagaku Zasshi,* 66: 127–129 (1963); Akashi, *Kogyo Kagaku Zasshi,* 66 (12):1909–12 (1963); and U.S. Pat. No. 3,165,486, Johnson, issued Jan. 12, 1965. However, these prior art vinyl itaconate derivatives have not been found to be as satisfactory in situ film-formers as those of the present invention; 1-vinyl itaconate has a relatively low rate of polymerization, while the divinyl itaconate exhibits too great a degree of crosslinking, due to its high number of unsaturated sites. The 4-vinyl itaconate derivatives described herein have been found to be good film-forming compounds, exhibiting advantages in this regard over the previously known itaconate derivatives.

SUMMARY OF THE INVENTION

The present invention encompasses compounds having a formula selected from the group consisting of

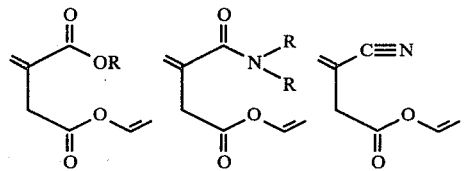

wherein R is selected from H, or $C_1$–$C_{18}$ alkyl, substituted alkyl, aryl or substituted aryl. R is preferably H or $C_1$–$C_6$ alkyl.

The invention also encompasses polymers prepared by the free radical polymerization of those compounds.

DETAILED DESCRIPTION OF THE INVENTION

The compounds of the present invention have a formula selected from

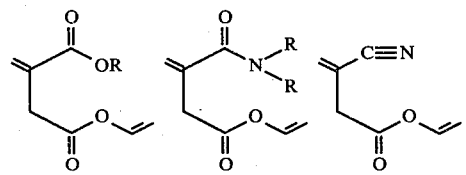

In this formula R may be hydrogen or an alkyl, substituted alkyl, aryl or substituted aryl having from 1 to 18 carbon atoms. Preferred compounds are those in which R is selected from hydrogen or $C_1$–$C_6$ alkyl, most preferably hydrogen, methyl or butyl. The preferred compounds are those having the formula

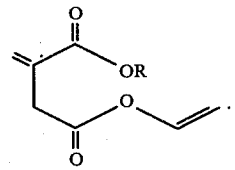

The acid compounds of the present invention (1) may be synthesized via the transvinylation of itaconic acid with vinyl acetate. This reaction is carried out at 25° C. using mercuric acetate and boron trifluoride etherate as catalysts. The reaction is set forth below.

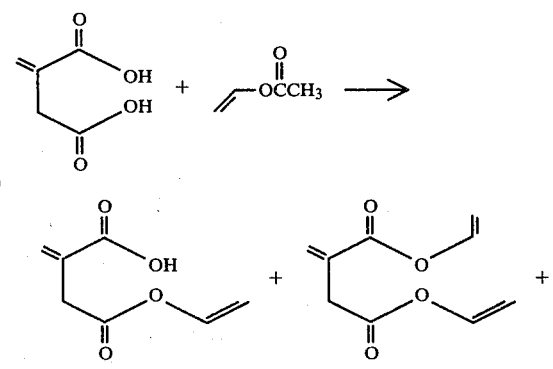

-continued

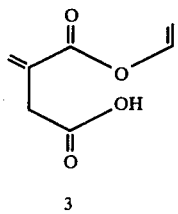

3

The reaction is very solvent dependent, with dimethoxyethane, tetrahydrofuran and acetone as the preferred solvents, tetrahydrofuran and dimethoxyethane being especially preferred. Other useful solvents include vinyl acetate and diethyl ether. Mixtures of these solvents may be used. Experiments have indicated that the use of a polar solvent accentuates the difference between the two itaconic acid carboxyl groups in the transvinylation reaction.

Compound 1 may then be converted to its corresponding esters by treatment first with thionyl chloride and second with pyridine and the desired alcohol.

4-Vinyl-2-methylene-1-amidobutanedioic acid, 4, was synthesized by a two-step sequence from 4-vinyl-2-methylenebutanedioic acid. The acid was converted to the corresponding acid chloride, 5, by reaction with thionyl chloride in methylene chloride. After purification by distillation, 5 was dissolved in diethyl ether and cooled to 0° C. while ammonia was bubbled into the solution until the resulting exothermic reaction ceased. The reaction mixture was then washed with water and evaporated to give a white powder, 4. This was recrystallized from hexane-ethyl acetate, mp 69°–70° C.

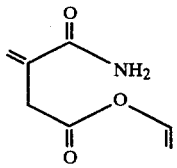 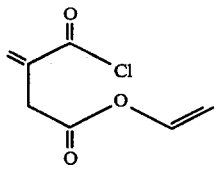

4  5

Formation of vinyl 3-cyanobut-3-enoate, 6, was carried out by dehydration of 4 with thionyl chloride in methylene chloride for one hour at reflux. Removal of the solvent gave a dark oil which was further purified by vacuum distillation.

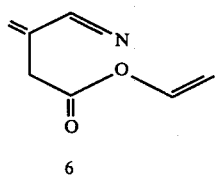

6

These compounds are useful as film-formers, such as in paints, coating compositions or plastic compositions. The unique cyclopolymerization mechanism which these compounds are believed to undergo makes them especially attractive for such use in a film-forming context. The free radical polymerization of the methyl ester of compound 1 has been found to take place at a very rapid rate compared with the polymerizations of vinyl hexanoate or dimethyl itaconate. The rate of polymerization is even faster than that of 1-vinyl-4-butyl-2-methylenebutanedioic acid by a factor of about 5. The relative polymerization rates are set forth in Table I.

The polymerization of the compounds of the present invention was carried out in the following manner. Approximately one gram of polymer was prepared by free radical polymerization of 5 g. of 4-vinyl-2-methylene-1-butanedioic acid (0.2 M) using 3 mole percent azobisisobutylnitrile (AIBN) in chlorobenzene at 60° C. Other useful solvents include benzene, ethyl acetate, and mixtures thereof. The polymerization may be carried out at temperatures between about 50° C. and 100° C. The reaction was followed by gas chromatography until 20% completion; the volatiles were then removed by vacuum pumping to give 5 grams of a jelly-like mass which was extracted with diethyl ether until a white powder remained. This material was then dissolved in tetrahydrofuran and precipitated using hexane. The polymer had a molecular weight of about 10,000 Daltons, as determined by high pressure liquid chromatography with $\mu$-styragel columns which were calibrated with polystryene and polyacrylate standards. An infrared spectrum (KBr pellet) contained two sharp carbonyl bands, 1730 and 1790 cm$^{-1}$, indicating a normal carbonyl and a 5-membered lactone. Also, the olefin bands at 1640 cm$^{-1}$ were essentially gone. This was in contrast to the polymer formed by the 1-vinyl-4-methyl-2-methylenebutanedioic acid which had only one carbonyl band (1740 cm$^{-1}$) and the olefin band at 1640 cm$^{-1}$ was still pronounced. It is believed that these spectroscopic differences, as well as the rapid rate of polymerization of the 4-vinyl-1-butyl compound, are accounted for by a 5-membered intramolecular/intermolecular cyclopolymerization which the 4-vinyl-1-butyl compound undergoes. The proposed mechanism for the cyclopolymerization is set forth below, with n having the value between about 20 and about 500, preferably between about 20 and about 70.

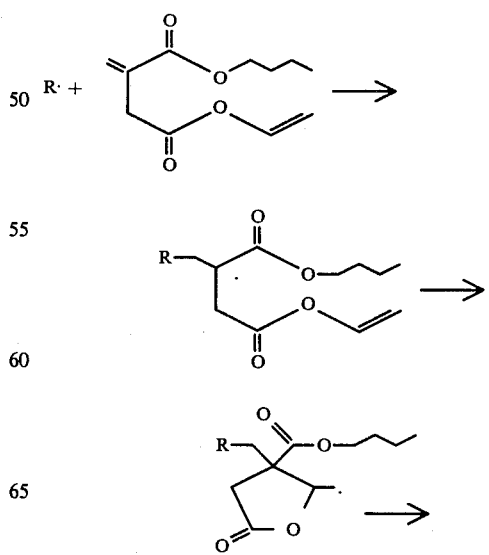

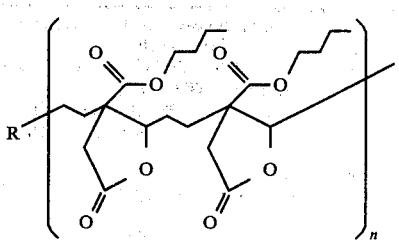

Polymers from the amide (4) and nitrile (6) analogues, discussed above, have the following formulae, wherein R and n are as previously defined.

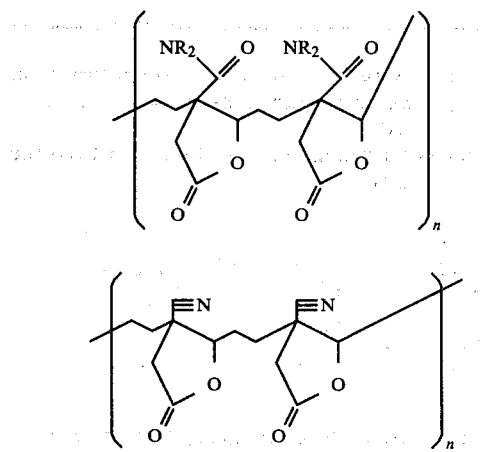

These polymers may be made using the same procedure as the 4-vinyl-2-methylene-1-butyl butanedioic acid polymer, described above.

TABLE I

| Relative Rates of Polymerization of 2-Methylenebutanedioic Esters | |
|---|---|
| Relative Rate (at 70° C.) | Compound |
| 1.0 | (structure with OMe, OMe) |
| 2.9 | (structure with O, OMe) |
| 14.6 | (structure with OMe, O-allyl) |
| 1.4 | $OC(CH_2)_4CH_3$ |

The compounds of the present invention may also be used in the formation of more complex polymer precursor materials. Thus, the compounds may be used as pendant groups, in which case R would be a low molecular weight polymeric backbone, such as a polyacrylate, polymethacrylate, polyester, polyurethane, polycarbonate, polyepoxide, polyvinyl or polystyrene having a molecular weight of from about 1,000 to about 10,000, with polyacrylate backbones being preferred. In this case, the polymeric resin material formed demonstrates outstanding in situ free radical polymerization capacity and is especially useful in the formation of paint and plastic compositions. Such polymer precursor materials are described and claimed in concurrently-filed U.S. patent application Ser. No. 290,918, Robbins and Bush, Agents for Preparing Cross-Linked Polymers and Paint and Plastic Compositions Containing Those Agents, incorporated herein by reference. For example, one such resin, using a low molecular weight methyl acrylate (MA):hydroxyethyl acrylate (HEA) backbone, in a 9MA:2HEA ratio, and beta-vinyl itaconyl chloride (B-VIC) as the pendant group, was formed using the reaction and reagents given below.

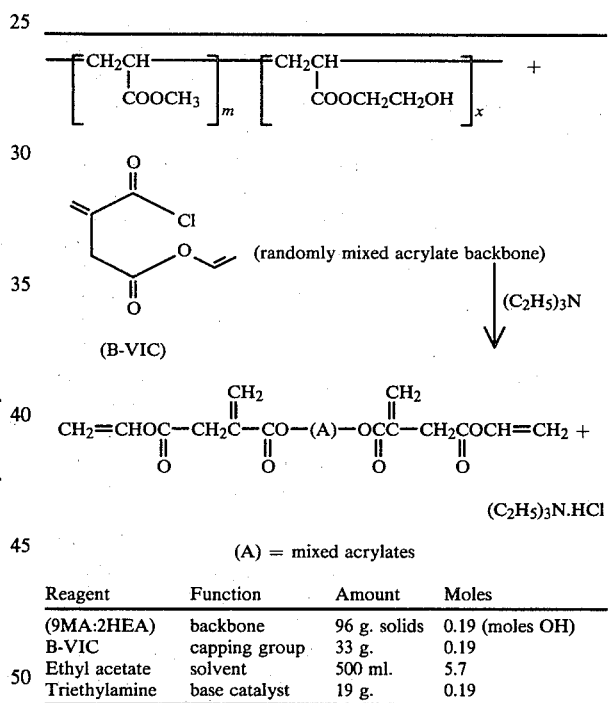

(A) = mixed acrylates

| Reagent | Function | Amount | Moles |
|---|---|---|---|
| (9MA:2HEA) | backbone | 96 g. solids | 0.19 (moles OH) |
| B-VIC | capping group | 33 g. | 0.19 |
| Ethyl acetate | solvent | 500 ml. | 5.7 |
| Triethylamine | base catalyst | 19 g. | 0.19 |

A two-liter, three-neck round bottom flask was fitted with the following: a Teflon stirring paddle, shaft and bearing for an overhead mechanical stirrer; a 250 milliliter addition funnel with a side arm; an argon inlet at the top of the addition funnel; a thermometer; and an argon outlet attached to a bubbler.

The flask was flushed with argon and an argon atmosphere was maintained during the reaction. The backbone resin in ethyl acetate, B-VIC, and ethyl acetate solvent were placed in the reaction flask. Vigorous stirring was begun and the drop-wise addition from the addition funnel of a solution of distilled triethylamine in an equal amount of ethyl acetate was begun. The triethylamine was distilled through a 12 inch Vigreux column at atmospheric pressure and the middle cut, boiling at 80° C., was used. To promote good mixing and dispersion of the triethylamine and to prevent gellation, it is important that the addition of this solution be slow. The addition step took about 2 hours. During the addition of the triethylamine, the amine hydrochloride formed precipitated as a white solid, giving the reaction mixture a white cloudy appearance. Toward the end of the addition, a more muddy appearance developed as the reaction mixture darkened. At this point, if the color becomes intense, the addition of triethylamine solution should be stopped. After the triethylamine addition is stopped or completed, the reaction should be worked up immediately.

The precipitated amine hydrochloride was filtered through a Buchner funnel with Whatman glass fiber paper using a lab aspirator (about 20 mm mercury). The filtration proceeded rapidly. The filter cake was then washed with 100 milliliters of ethyl acetate. A 10 milliliter aliquot of the ethyl acetate filtrate was concentrated on a rotovap and was used for an NMR spectrum. The rest of the solution was transferred to a 2 liter separatory funnel and washed with an equal volume of saturated sodium bicarbonate solution. An emulsion was formed and several hours was required for a clean, distinct separation of phases. The mixture was allowed to stand overnight to separate. The lower layer still contained some insoluble polymer, but was easily separated from the upper layer. The lower layer consisted of the aqueous phase which was drawn away and discarded. The upper organic phase was drawn into a 2 liter Erlenmeyer flask and 100 grams of anhydrous magnesium sulfate was added and allowed to stand for half an hour. The magnesium sulfate was then filtered out through a Buchner funnel with glass fiber paper. The resulting ethyl acetate solution was then concentrated on a rotovap ($H_2O$ aspirator, 20 mm mercury, 40° C.) to the desired solids level, approximately 75–85% solids. The solids level was determined by the following ASTM method of evaporation at 100° C. for two hours: a sample of the concentrated resin was accurately weighed (to 4 decimal places) into a glass Petri dish, placed in the oven at 100° C. for two hours, cooled to room temperature and reweighed.

The resin was transferred to a bottle and stored under argon at 0° C. It is important that oxygen be excluded to prevent premature polymerization of the resin. The product was then analyzed by NMR (in $CDCl_3$) and IR (neat with residual ethyl acetate). In the infrared spectrum, the vinyl group is seen at 1640 cm$^{-1}$. The NMR spectrum showed the following peaks (chemical shifts reported in δ):

| | |
|---|---|
| 1.73 | two broad peaks for the hydroxy ethyl acrylate |
| 2.33 | portion of the backbone |
| 3.47 | singlet 2H, >CH$_2$ (from B-itaconate methylene) |
| 3.67 | singlet 3H, (CO$_2$CH$_3$)$_9$ |
| [4.33 | singlet 2H, >CH$_2$ (from alpha-itaconate methylene side product)] |
| 4.53 | |
| 4.63 | |
| 4.73 | doublets 2H, —CH=CH$_2$ |
| 5.00 | |
| 5.83 | singlet 1H each 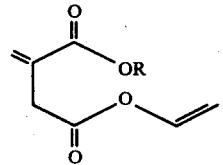 |
| 6.37 | singlet |
| 7.03 | |
| 7.13 | |
| 7.27 | quartet 1H, —CH=CH$_2$ |
| 7.37 | |

This resin may be used as an in situ film-former in formulating paint, coating and plastic compositions.

What is claimed is:

1. A compound having a formula selected from the group consisting of

wherein R is selected from the group consisting of H, $C_1$–$C_{18}$ alkyl, and $C_6$–$C_{18}$ aryl.

2. A compound according to claim 1 having the formula

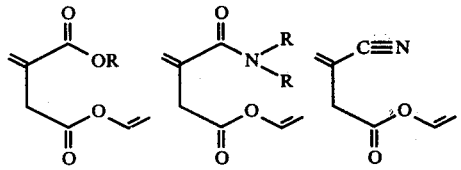

3. A compound according to claim 2 wherein R is selected from the group consisting of H and $C_1$–$C_6$ alkyl.

4. A compound according to claim 3 wherein R is selected from the group consisting of H, methyl and butyl.

* * * * *